(12) United States Patent
Shakespeare

(10) Patent No.: US 7,880,156 B2
(45) Date of Patent: Feb. 1, 2011

(54) SYSTEM AND METHOD FOR Z-STRUCTURE MEASUREMENTS USING SIMULTANEOUS MULTI-BAND TOMOGRAPHY

(75) Inventor: John F. Shakespeare, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 110 days.

(21) Appl. No.: 11/646,097

(22) Filed: Dec. 27, 2006

(65) Prior Publication Data

US 2008/0157013 A1  Jul. 3, 2008

(51) Int. Cl.
*G01N 21/86* (2006.01)
*G01J 3/50* (2006.01)

(52) U.S. Cl. .................... 250/559.4; 250/226

(58) Field of Classification Search ...............
250/559.04–559.08, 559.19, 559.22, 559.26–559.28,
250/559.4–559.46, 221, 226; 382/141; 356/600,
356/601, 630, 635, 625, 429–431, 445, 237.1,
356/237.2, 238.1–238.3, 239.1, 239.7
See application file for complete search history.

(56) References Cited

U.S. PATENT DOCUMENTS

| | | |
|---|---|---|
| 3,536,405 A | 10/1970 | Flower |
| 3,802,774 A | 4/1974 | Eschler et al. |
| 4,068,955 A | 1/1978 | Bodlaj |
| 4,160,204 A | 7/1979 | Holmgren et al. |
| 4,276,480 A | 6/1981 | Watson |
| 4,311,658 A | 1/1982 | Nicoll |
| 4,490,845 A | 12/1984 | Steinbruegge et al. |
| 4,505,550 A | 3/1985 | Steinbruegge |
| 4,708,483 A | 11/1987 | Lorenz |
| 4,773,760 A | 9/1988 | Makkonen |
| 4,797,246 A | 1/1989 | Reinke et al. |
| 4,843,481 A | 6/1989 | Plummer |
| 4,879,471 A | 11/1989 | Dahlquist |
| 4,885,709 A | 12/1989 | Edgar et al. |
| 5,013,403 A | 5/1991 | Chase |
| 5,015,070 A * | 5/1991 | Montgomery et al. ....... 359/851 |
| 5,039,855 A | 8/1991 | Kemeny et al. |
| 5,094,535 A | 3/1992 | Dahlquist et al. |

(Continued)

FOREIGN PATENT DOCUMENTS

DE  100 31 636 A1  1/2002

(Continued)

*Primary Examiner*—Que T Le
*Assistant Examiner*—Pascal M Bui Pho
(74) *Attorney, Agent, or Firm*—Munck Carter, LLP

(57) ABSTRACT

A method includes simultaneously illuminating a material using multiple first radiances and measuring multiple second radiances from the material. Each second radiance includes at least a portion of two or more first radiances that have interacted with the material. The method also includes determining a structure of the material based on the measurements. The first radiances may be directed at the material from different directions, and the second radiances may be measured at different positions around the material. The structure of the material could be determined by determining at least one of a scattering profile and an absorption profile. If the material includes a sheet of paper, a boundary between two layers in the sheet of paper could be identified by a discontinuity in the scattering profile, and a non-uniform distribution of a filler in the sheet of paper could be identified by a smooth variation in the scattering profile.

21 Claims, 3 Drawing Sheets

U.S. PATENT DOCUMENTS

| Patent No. | Type | Date | Inventor | Ref |
|---|---|---|---|---|
| 5,166,748 | A | 11/1992 | Dahlquist | |
| 5,172,005 | A * | 12/1992 | Cochran et al. | 250/559.08 |
| 5,210,593 | A | 5/1993 | Kramer | |
| 5,230,923 | A | 7/1993 | Hirokawa et al. | |
| 5,235,192 | A | 8/1993 | Chase et al. | |
| 5,276,327 | A | 1/1994 | Bossen et al. | |
| 5,365,084 | A * | 11/1994 | Cochran et al. | 250/559.02 |
| 5,438,406 | A | 8/1995 | Puschell | |
| 5,444,528 | A | 8/1995 | Puschell | |
| 5,492,601 | A | 2/1996 | Ostermayer et al. | |
| 5,541,413 | A | 7/1996 | Pearson et al. | |
| 5,581,353 | A * | 12/1996 | Taylor | 356/631 |
| 5,598,266 | A * | 1/1997 | Cornuejols | 356/367 |
| 5,606,173 | A | 2/1997 | Concannon et al. | |
| 5,694,214 | A | 12/1997 | Watanabe et al. | |
| 5,696,591 | A * | 12/1997 | Bilhorn et al. | 356/429 |
| 5,714,763 | A | 2/1998 | Chase et al. | |
| 5,795,394 | A | 8/1998 | Belotserkovsky et al. | |
| 5,821,536 | A | 10/1998 | Pettit | |
| 5,891,306 | A | 4/1999 | Chase et al. | |
| 6,031,233 | A | 2/2000 | Levin et al. | |
| 6,038,028 | A | 3/2000 | Grann et al. | |
| 6,100,986 | A | 8/2000 | Rydningen | |
| 6,111,649 | A | 8/2000 | Tominaga et al. | |
| 6,122,042 | A * | 9/2000 | Wunderman et al. | 356/73 |
| 6,144,446 | A * | 11/2000 | Nagasaki et al. | 356/237.3 |
| 6,262,419 | B1 | 7/2001 | Huth-Fehre et al. | |
| 6,281,679 | B1 | 8/2001 | King et al. | |
| 6,289,600 | B1 | 9/2001 | Watts | |
| 6,297,879 | B1 | 10/2001 | Yang et al. | |
| 6,327,374 | B1 * | 12/2001 | Piironen et al. | 382/108 |
| 6,437,357 | B1 * | 8/2002 | Weiss et al. | 250/559.4 |
| 6,441,905 | B1 | 8/2002 | Tojyo et al. | |
| 6,459,488 | B1 | 10/2002 | Heffner | |
| 6,476,920 | B1 | 11/2002 | Scheiner et al. | |
| 6,494,446 | B1 | 12/2002 | Tomiyama et al. | |
| 6,515,746 | B2 | 2/2003 | Opsal et al. | |
| 6,538,751 | B2 * | 3/2003 | Ono | 356/614 |
| 6,556,306 | B2 | 4/2003 | Jiang et al. | |
| 6,565,343 | B1 | 5/2003 | Krycki | |
| 6,573,999 | B1 | 6/2003 | Yang | |
| 6,639,201 | B2 | 10/2003 | Almogy et al. | |
| 6,643,060 | B2 | 11/2003 | Hashimoto et al. | |
| 6,646,752 | B2 | 11/2003 | Chen et al. | |
| 6,690,357 | B1 | 2/2004 | Dunton et al. | |
| 6,700,370 | B2 | 3/2004 | Chen et al. | |
| 6,731,380 | B2 | 5/2004 | Amara et al. | |
| 6,731,384 | B2 * | 5/2004 | Ohshima et al. | 356/237.2 |
| 6,743,337 | B1 * | 6/2004 | Ischdonat | 162/198 |
| 6,744,052 | B1 | 6/2004 | Petersson et al. | |
| 6,757,069 | B2 | 6/2004 | Bowles | |
| 6,762,846 | B1 | 7/2004 | Poris | |
| 6,780,284 | B2 | 8/2004 | Almi et al. | |
| 6,793,854 | B1 | 9/2004 | Kirjavainen | |
| 6,816,636 | B2 | 11/2004 | Cole et al. | |
| 6,822,785 | B1 | 11/2004 | Chu et al. | |
| 6,849,844 | B2 | 2/2005 | Khoury | |
| 7,345,747 | B2 * | 3/2008 | Hillmann et al. | 356/71 |
| 7,369,240 | B1 * | 5/2008 | Abbott et al. | 356/429 |
| 2001/0012107 | A1 * | 8/2001 | Toh | 356/601 |
| 2003/0007161 | A1 | 1/2003 | Bowles | |
| 2004/0124366 | A1 | 7/2004 | Zeng et al. | |
| 2004/0207839 | A1 * | 10/2004 | Gerstner et al. | 356/239.1 |
| 2004/0246493 | A1 | 12/2004 | Kim et al. | |
| 2005/0018183 | A1 * | 1/2005 | Shortt | 356/239.1 |
| 2005/0187478 | A1 | 8/2005 | Beaudry et al. | |
| 2006/0132796 | A1 | 6/2006 | Haran | |
| 2006/0132808 | A1 | 6/2006 | Jasinski et al. | |
| 2006/0164643 | A1 | 7/2006 | Giakos | |

FOREIGN PATENT DOCUMENTS

| | | |
|---|---|---|
| EP | 0 843 155 A1 | 5/1998 |
| WO | WO 87/07381 | 12/1987 |
| WO | WO 97/08537 A1 | 3/1997 |
| WO | WO 99/02941 A1 | 1/1999 |
| WO | WO 00/31521 A1 | 6/2000 |
| WO | WO 2006/116672 A2 | 11/2006 |

* cited by examiner

SYSTEM AND METHOD FOR Z-STRUCTURE MEASUREMENTS USING SIMULTANEOUS MULTI-BAND TOMOGRAPHY

TECHNICAL FIELD

This disclosure relates generally to measurement systems and more specifically to a system and method for Z-structure measurements using simultaneous multi-band tomography.

BACKGROUND

Sheets of material are often used in various industries and in a variety of ways. These materials can include paper, plastic, and other materials manufactured or processed in webs or sheets. As a particular example, long sheets of paper or other single layer or multi-layer products can be manufactured and collected in reels.

The "Z-structure" or cross-sectional structure of paper and other sheet materials is often a determining factor in numerous quality properties for the materials. For example, the distribution of voids between fibers in paper products typically affects bulk and opacity, and the distribution of fillers in paper products typically affects printing quality. Only fillers near the surface typically affect surface smoothness and ink permeability, and asymmetric filler distribution can cause the color of the surfaces of a paper sheet to differ.

Papermakers are often interested in the distribution of fillers because there are several process adjustments available to influence it. As a result, accurate measurements of the Z-structure of a paper sheet could lead to the identification of filler distribution problems and allow timely adjustments to the paper-making process. Another issue may arise for intrinsically multi-layer sheets of material, such as those formed by splicing together multiple formed sheets or by coating a formed sheet with a polymer. In these cases, it is often desirable to know the thicknesses of individual layers or differences between exterior layers and interior layers.

SUMMARY

This disclosure provides a system and method for Z-structure measurements using simultaneous multi-band tomography.

In a first embodiment, a method includes simultaneously illuminating a material using multiple first radiances. The method also includes measuring multiple second radiances from the material. Each second radiance includes at least a portion of two or more first radiances that have interacted with the material. In addition, the method includes determining a structure of the material based on the measurements of the second radiances.

In particular embodiments, the first radiances are directed at the material from different directions, and the second radiances are measured at different positions around the material.

In other particular embodiments, measuring the multiple second radiances includes simultaneously measuring the multiple second radiances from the material.

In yet other particular embodiments, determining the structure of the material includes determining at least one of a scattering profile and an absorption profile based on the measurements of the second radiances. Also, the material could include a sheet of paper. A boundary between two layers in the sheet of paper could be identified by a discontinuity in the scattering profile. A non-uniform distribution of a filler in the sheet of paper could be identified by a smooth variation in the scattering profile.

In a second embodiment, a system includes a plurality of radiance sources operable to simultaneously illuminate a material using multiple first radiances. The system also includes a plurality of sensors operable to measure multiple second radiances from the material. Each second radiance includes at least a portion of two or more first radiances that have interacted with the material. In addition, the system includes a controller operable to determine a structure of the material based on the measurements of the second radiances.

In a third embodiment, a computer program is embodied on a computer readable medium and is operable to be executed. The computer program includes computer readable program code for controlling a plurality of radiance sources. The radiance sources are operable to simultaneously illuminate a material using multiple first radiances. The computer program also includes computer readable program code for receiving measurements from a plurality of sensors. The measurements identify multiple second radiances from the material, where each second radiance includes at least a portion of two or more first radiances that have interacted with the material. In addition, the computer program includes computer readable program code for determining a structure of the material based on the measurements of the second radiances.

In a fourth embodiment, a sheet production system includes a sheet machine operable to manufacture and/or process a sheet of material and a sensor arrangement. The sensor arrangement is operable to simultaneously illuminate the sheet using multiple first radiances and measure multiple second radiances from the sheet. Each second radiance includes at least a portion of two or more first radiances that have interacted with the sheet. The sensor arrangement is also operable to determine a structure of the sheet based on the measurements of the second radiances.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
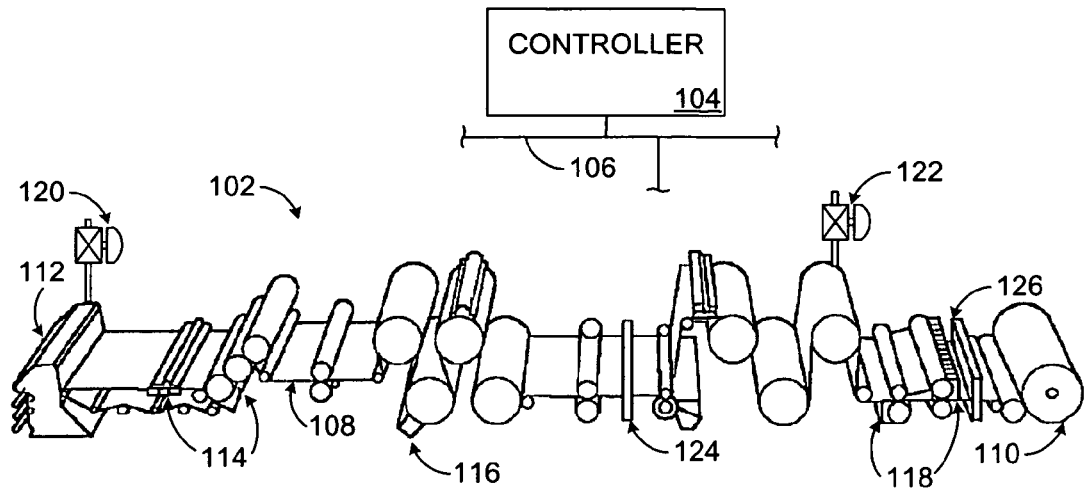
FIG. 1 illustrates an example paper production system according to one embodiment of this disclosure.

FIG. 1 illustrates an example paper production system 100 according to one embodiment of this disclosure. The embodiment of the paper production system 100 shown in FIG. 1 is for illustration only. Other embodiments of the paper production system 100 may be used without departing from the scope of this disclosure.

In this example, the paper production system 100 includes a paper machine 102, a controller 104, and a network 106. The paper machine 102 includes various components used to produce a paper product. In this example, the various components may be used to produce a paper sheet 108 collected at a reel 110. The controller 104 monitors and controls the operation of the paper machine 102, which may help to maintain or increase the quality of the paper sheet 108 produced by the paper machine 102.

As shown in FIG. 1, the paper machine 102 includes a headbox 112, which distributes a pulp suspension uniformly across the machine onto a continuous moving wire screen or mesh. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the sheet. The dilution water may be used to help ensure that the resulting paper sheet 108 has a more uniform basis weight across the sheet 108. The headbox 112 may also include an array of slice lip actuators, which controls a slice opening across the machine from which the pulp suspension exits the headbox 112 onto the moving wire screen or mesh. The array of slice lip actuators may also be used to control the basis weight of the paper or the distribution of fiber orientation angles of the paper across the sheet 108.

An array of steam actuators 114 produces hot steam that penetrates the paper sheet 108 and releases the latent heat of the steam into the paper sheet 108, thereby increasing the temperature of the paper sheet 108 in sections across the sheet. The increase in temperature may allow for easier removal of water from the paper sheet 108. An array of rewet shower actuators 116 adds small droplets of water (which may be air atomized) onto the surface of the paper sheet 108. The array of rewet shower actuators 116 may be used to control the moisture profile of the paper sheet 108, reduce or prevent over-drying of the paper sheet 108, or correct any dry streaks in the paper sheet 108.

The paper sheet 108 is then often passed through a calendar having several nips of counter-rotating rolls. Arrays of induction heating actuators 118 heat the shell surfaces of various ones of these rolls. As each roll surface locally heats up, the roll diameter is locally expanded and hence increases nip pressure, which in turn locally compresses the paper sheet 108. The arrays of induction heating actuators 118 may therefore be used to control the caliper (thickness) profile of the paper sheet 108. The nips of a calendar may also be equipped with other actuator arrays, such as arrays of air showers or steam showers, that may be used to control the gloss profile or smoothness profile of the paper sheet.

Two additional actuators 120-122 are shown in FIG. 1. A thick stock flow actuator 120 controls the consistency of the incoming pulp received at the headbox 112. A steam flow actuator 122 controls the amount of heat transferred to the paper sheet 108 from drying cylinders. The actuators 120-122 could, for example, represent valves controlling the flow of pulp and steam, respectively. These actuators may be used for controlling the dry weight and moisture of the paper sheet 108. Additional components could be used to further process the paper sheet 108, such as a supercalender for improving the paper sheet's thickness, smoothness, and gloss or one or more coating stations each applying a layer of coatant to a surface of the paper to improve the smoothness and printability of the paper sheet. Similarly, additional flow actuators may be used to control the proportions of different types of pulp and filler material in the thick stock and to control the amounts of various additives, such as retention aid or dyes, that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process the produced paper or with systems that produce or process other items or materials, such as plastic, textiles, metal foil or sheets, or other or additional materials.

In order to control the paper-making process, properties of the paper sheet 108 may be continuously or repeatedly measured and the paper machine 102 adjusted to ensure sheet quality. This control may be achieved by measuring one or more sheet properties at various stages in the manufacturing process. This information may then be used to adjust various actuators within the paper machine 102 to compensate for any variations of the sheet properties from desired targets.

As shown in FIG. 1, the paper machine 102 includes two scanners 124-126, each of which may include one or more sensors. The scanners 124-126 are capable of scanning the paper sheet 108 and measuring one or more characteristics of the paper sheet 108. For example, the scanners 124-126 could include sensors for measuring the weight, moisture, caliper (thickness), gloss, smoothness, or any other or additional characteristics of the paper sheet 108.

Figure 2:
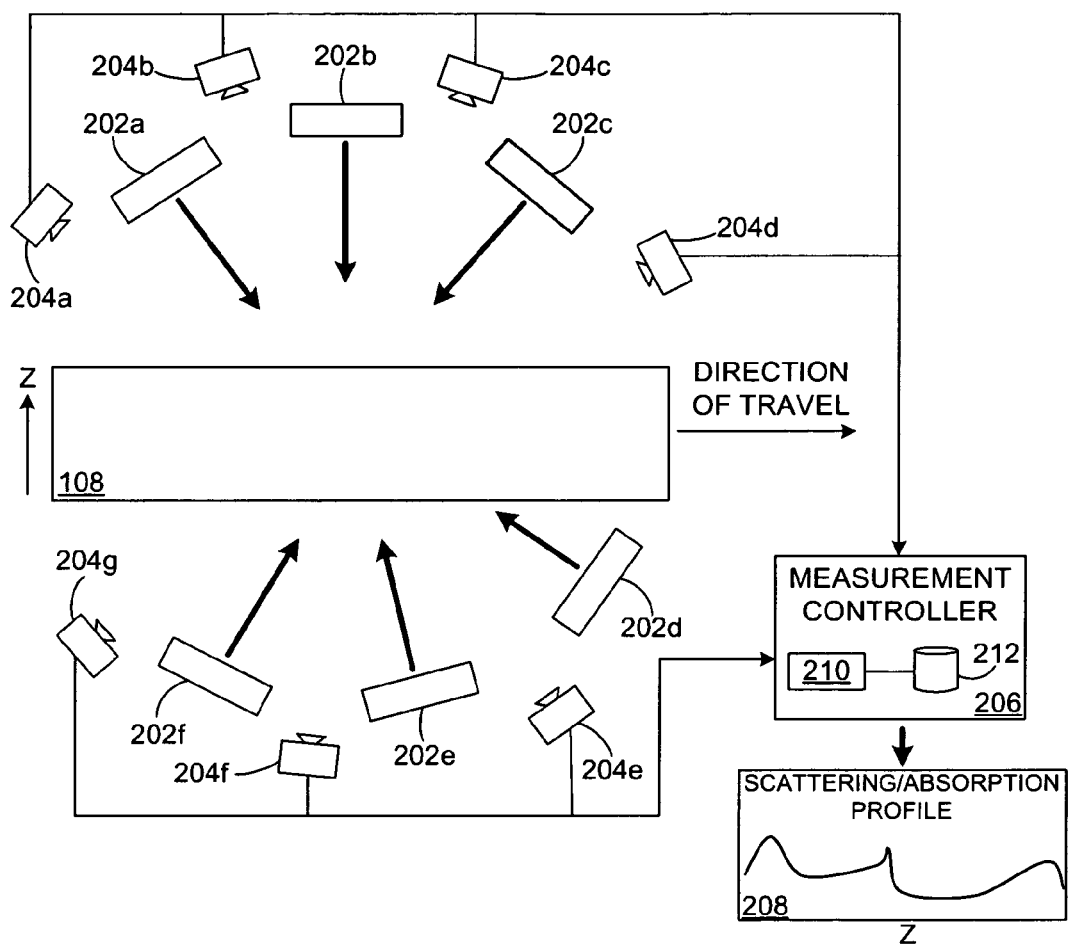
FIG. 2 illustrates an example sensor arrangement for Z-structure measurements using simultaneous multi-band tomography according to one embodiment of this disclosure.

As described in more detail below, at least one of the scanners 124-126 could include sensors and other components for determining the Z-structure of the paper sheet 108. For example, at least one of the scanners 124-126 could include a set of radiance sources (light sources) for illuminating the paper sheet 108 and a set of sensors (such as spectrometric detectors) for measuring the radiance reflected off of and/or transmitted through the paper sheet 108. These measurements can be used to detect scattering or absorption of light by the paper sheet 108, which can then be used to determine the Z-structure of the paper sheet 108. One example embodiment of this arrangement is shown in FIG. 2, which is described below.

Each of the scanners 124-126 includes any suitable structure or structures for measuring or detecting one or more characteristics of the paper sheet 108, such as sets or arrays of sensors. A scanning or moving set of sensors represents one particular embodiment for measuring sheet properties. Other embodiments could be used, such as those using stationary sets or arrays of sensors.

The controller 104 receives measurement data from the scanners 124-126 and uses the data to control the paper machine 102. For example, the controller 104 may use the measurement data to adjust the various actuators in the paper machine 102 so that the paper sheet 108 has properties at or near desired properties. The controller 104 could also use the measurement data to determine the Z-structure of the paper sheet 108, which may allow the controller 104 to adjust the operation of the paper machine 102 if necessary. The controller 104 includes any hardware, software, firmware, or combination thereof for controlling the operation of at least part of the paper machine 102. In particular embodiments, the controller 104 may represent a proportional-integral-derivative (PID) controller or a cross-direction machine-direction (CDMD) model predictive controller (MPC).

The network 106 is coupled to the controller 104 and various components of the paper machine 102 (such as the actuators and the scanners 124-126). The network 106 facilitates communication between components of system 100. The network 106 represents any suitable network or combination of networks facilitating communication between components in the system 100. The network 106 could, for example, represent an Ethernet network, an electrical signal network (such as a HART or FOUNDATION FIELDBUS network), a pneumatic control signal network, or any other or additional network(s).

Although FIG. 1 illustrates one example of a paper production system 100, various changes may be made to FIG. 1. For example, other systems could be used to produce paper products or other products. Also, while shown as including a single paper machine 102 with various components and a single controller 104, the production system 100 could include any number of paper machines or other production machinery having any suitable structure, and the system 100 could include any number of controllers. In addition, FIG. 1 illustrates one operational environment in which the Z-structure of a sheet material can be determined. This functionality could be used in any other suitable system.

FIG. 2 illustrates an example sensor arrangement 200 for Z-structure measurements using simultaneous multi-band tomography according to one embodiment of this disclosure. The embodiment of the sensor arrangement 200 shown in FIG. 2 is for illustration only. Other embodiments of the sensor arrangement 200 could be used without departing from the scope of this disclosure. Also, for ease of explanation, the sensor arrangement 200 in FIG. 2 is described as forming at least part of the scanner 126 in the paper production system 100 of FIG. 1. The sensor arrangement 200 could be used in any other or additional location in the system 100 or in any other system. The sensor arrangement 200 could also be used to determine the Z-structure of any suitable material and is not limited to use with a paper sheet 108.

In general, tomography is a process for identifying the internal structure and arrangement of an object (such as a human body). Tomography typically involves observing the effects of the passage of waves (such as X-rays) through the object and is routinely used in medical and other applications. However, conventional tomographic techniques typically involve making sequential measurements of an object, which is often difficult (if not impossible) for a moving object such as a moving paper sheet 108. As described below, the sensor arrangement 200 supports the use of tomography to determine the Z-structure of a paper sheet 108 or other material, even when the paper sheet 108 or other material is moving.

In this example, the sensor arrangement 200 illuminates a paper sheet 108 and measures the radiance reflected off of and/or transmitted through the paper sheet 108. These measurements can then be used to determine the Z-structure of the paper sheet 108.

As shown in FIG. 2, the sensor arrangement 200 includes multiple radiance sources 202a-202f and multiple sensors 204a-204g. The radiance sources 202a-202f produce radiance or light for illuminating the paper sheet 108. Each of the radiance sources 202a-202f includes any suitable structure for generating radiance for illuminating the paper sheet 108 or other material. For example, each of the radiance sources 202a-202f could include one or more light emitting diodes (LEDs), lasers, or masers. Each radiance source may also include optical elements, such as lenses, mirrors, masks, pinholes, beam expanders, or the like, to produce a light beam of suitable geometry. In particular embodiments, each of the radiance sources 202a-202f produces a monochrome or near-monochrome beam of essentially collimated light. In these embodiments, each of the radiance sources 202a-202f could generate light at a wavelength or range of wavelengths that is unique to that radiance source.

The sensors 204a-204g measure radiance reflected off of and/or transmitted through the paper sheet 108. The sensors 204a-204g may measure the radiance in any suitable manner, such as by dividing any received radiance into multiple wavelength bands and measuring the radiance in each band. Each of the sensors 204a-204g includes any suitable structure for measuring radiance that has interacted with a paper sheet 108 or other material, such as a multi-wavelength spectrometric detector or an image detector comprising plural pixels each responsive to a particular range of wavelengths. In some embodiments, each of the sensors 204a-204g could also include suitable optics or other structures to gather radiances from the paper sheet 108 or other material.

Measurements from the sensors 204a-204g are provided to a measurement controller 206. The measurement controller 206 uses measurement data from the sensors 204a-204g to determine the Z-structure of the paper sheet 108. For example, the measurement controller 206 could determine and output one or more profiles 208, which in this example identifies how light is scattered or absorbed at different Z depths of the paper sheet 108. The profile(s) 208 could be used to identify discontinuities in the paper sheet 108, which could represent boundaries of different layers or non-uniform distribution of fillers in the paper sheet 108. Other or additional types of profiles 208 could also be generated by the measurement controller 206. The measurement controller 206 includes any hardware, software, firmware, or combination thereof for determining the Z-structure of a paper sheet 108 or other material. As an example, the measurement controller 206 could include one or more processors 210 and one or more memories 212 storing data and instructions used by the processor(s) 210. In particular embodiments, the measurement controller 206 could form part of the controller 104 in FIG. 1, or the measurement controller 206 could reside external to and interact with the controller 104.

In this example, each of the sensors 204a-204g is coupled to the measurement controller 206 using a wired connection (such as a wired network). One, some, or all of the sensors 204a-204g could also communicate with the measurement controller 206 using wireless communications. Moreover, each of the radiance sources 202a-202f could be coupled to or otherwise communicate with the measurement controller 206, which may allow the measurement controller 206 to control the illumination of the paper sheet 108.

In one aspect of operation, the radiance sources 202a-202f may illuminate the same general area of the paper sheet 108. The radiance sources 202a-202f illuminate the paper sheet 108 using multiple wavelengths or wavelength bands simultaneously. For example, each radiance source may generate monochrome or near-monochrome light, and the paper sheet 108 may be illuminated using intense pulses of light from all of the radiance sources 202a-202f. Each beam of light generated by a radiance source could be collimated or nearly collimated and have a small divergence angle. Each beam of light may also be essentially or substantially uniform over its cross-section, be polarized or unpolarized, and be coherent or noncoherent. The beams of light from the radiance sources 202a-202f could be pulsed simultaneously with one another, or the beams could be continuously generated. The beams of light could include near infrared, ultraviolet, visible, or any other light.

Each radiance source may illuminate the paper sheet 108 at a different angle, direction, or geometry. For each direction, a narrow band of wavelengths could be used, where no wavelengths are shared with any other direction. The radiance sources 202a-202f can be angularly distributed, either uniformly or non-uniformly, all around the paper sheet 108 or confined to one or more ranges. In particular embodiments, the radiance sources 202a-202f are arranged within a single plane, which may be substantially perpendicular to the moving sheet.

The sensors 204a-204g measure the radiances scattered/transmitted by the paper sheet 108 from numerous viewing angles. The sensors 204a-204g may detect multiple wavelengths or wavelength bands at various geometries (such as known directions) around the paper sheet 108 simultaneously. The sensors 204a-204g may be angularly distributed, uniformly or non-uniformly, all around the paper sheet 108 or confined to one or more angle ranges. The sensors 204a-204g may or may not be located in the same plane as the radiance sources 202a-202f. Each of the sensors 204a-204g may be responsive to some or all wavelengths or wavelength bands used in the illumination of the paper sheet 108.

Each of the sensors 204a-204g may receive radiance from essentially or substantially the same area of the paper sheet 108 at one or more angles. Each sensor could disperse its received radiance at each angle into a set of wavelength bands, which could correspond to the wavelength bands used by the radiance sources 202a-202f. Each sensor may then measure the radiance at each wavelength band. In particular embodiments, each sensor represents an image detector, where one image axis corresponds to the set of angles and the other axis corresponds to the set of wavelength bands. In other particular embodiments, each sensor represents an image detector in which each pixel is responsive to a particular wavelength band, and pixels responsive to each particular wavelength band are distributed across the image detector.

The measurement controller 206 receives the measurements from the sensors 204a-204g and generates one or more profiles 208 using the measurements. For example, the measurement controller 206 can use the received measurements to generate one or more scattering or absorption profiles 208, which can be used to determine or estimate the internal structure of the paper sheet 108. Among other things, this may allow internal boundaries, filler distribution, and void distribution of the paper sheet 108 to be inferred or determined. Here, the internal boundaries could represent boundaries between layers in multi-ply sheets or between a sheet and polymer coating layers. Also, the scattering distribution within the paper sheet 108 could help to identify the distribution of fillers and voids. Micron to multi-micron resolution could be supported depending, among other things, on the wavelengths used to illuminate the paper sheet 108.

In these embodiments, the measurements made for each wavelength or wavelength band represent the radiance scattered from a single illumination direction associated with a single radiance source 202a-202f. The measurements made by the sensors 204a-204g at each wavelength or wavelength band may therefore correspond to one step of a conventional tomography scan. Simultaneous measurements of multiple wavelengths or wavelength bands from multiple directions may therefore correspond to multiple steps of a tomography scan that are performed simultaneously by the sensor arrangement 200. The sensor arrangement 200 therefore supports partial tomographic measurements by simultaneously using multiple wavelengths or wavelength bands for illumination and imaging. This allows a scan of the paper sheet 108 across the measurement geometries to be simultaneous rather than sequential as in conventional tomography.

The simultaneous measurements can be analyzed by the measurement controller 206 in any suitable manner to determine the Z-structure of the paper sheet 108. For example, using methods from diffuse optical tomography, the measurement controller 206 may analyze an ensemble of wavelength measurements to determine the internal structure of the paper sheet 108. With a simultaneous scan, it is possible to compute within certain constraints the positions of discontinuities within the paper sheet 108 (which may reveal layer thicknesses) and the distribution of scattering power within the sheet 108 (which may reveal distribution of fillers and voids). Discontinuities in the scattering (or large changes over short distances) may reveal boundaries between layers in the sheet 108, while smoother variations may reveal non-uniformity of filler distribution in the sheet 108. Here, the intrinsic scattering of candidate constituents may be known in advance for each wavelength (if they differ). Also, the analysis may be bounded or constrained, such as when candidate solutions are confined to superpositions of planar laminates (regularization). If sufficient data quality exists, candidate solutions may include more complex geometric elements As a particular example, the set of wavelengths or wavelength bands may be scattered by the paper sheet 108, and this scattering may occur differently at different depths in the paper sheet 108 due to differences in composition or structure. The scattering properties of each constituent of the paper sheet 108 may be similar for all wavelengths or wavelength bands in the set. Knowledge of differences in scattering properties between wavelengths or wavelength bands could be used to refine a computed Z-structure determination or to produce uncertainty estimates for the Z-structure determination.

Depending on the material being analyzed and the implementation, absorption and fluorescent emission of the paper sheet 108 at any illumination wavelength may be negligible compared to the scattering effect. However, it is possible to employ detected fluorescent emission at a non-illumination wavelength due to excitation by an illumination wavelength.

In other embodiments, the absorption effect of the paper sheet 108 may be greater than the scattering effect, and the absorption effect can be used to determine the Z-structure of the paper sheet 108. In these embodiments, the scattering effect may be negligible, and the computational methods used by the measuring controller 206 and the layout of the sensor arrangement 200 may be different. For example, a sensor for each wavelength band may be placed opposite the corresponding radiance source for that wavelength band. This may allow computation of an absorption profile 208 rather than a scattering profile 208.

As noted above, the computation of a scattering profile 208 or other Z-structure from the detected radiances may be constrained. For example, the computations may be constrained to use bases that have sufficiently strong support in both the illumination and detection geometries. In particular embodiments, the computations may be constrained using a least squares approach with some normalization (such as the smoothest solution).

The sensor arrangement 200 shown in FIG. 2 could be deployed in any suitable manner in a system or device. For example, the sensor arrangement 200 could form part of a traversing sensor platform that moves across a paper sheet 108, such as on the scanner 126. The sensor arrangement 200 could also be placed in a fixed location over the paper sheet 108. In addition, the sensor arrangement 200 could represent an array of devices at different locations across the sheet 108.

The technique implemented using the sensor arrangement 200 has been described as using diffuse optical measurements, but it could also be applied to any range of spectral bands for which suitable illuminators and detectors are available. Depending on the implementation, it may be advantageous to use image detectors in optical bands and to use non-imaging detectors in other bands. Similarly, while described as taking measurements of a moving paper sheet 108, the sensor arrangement 200 is not restricted to that field. It could be adapted to measure arbitrarily-shaped objects of any suitable material or materials (whether moving or stationary), provided suitable wavelengths or wavelength bands and intensities can be used.

The results of the analysis performed by the measurement controller 206 could be used in any suitable manner. For example, in the system 100 of FIG. 1, a profile 208 could be used by the controller 104 to change the headbox consistency, rush-drag, or suction in the paper machine 102. These may affect the rate of dewatering of the paper sheet 108 and change the paper sheet's Z-structure. The profile 208 could also be used by the controller 104 to adjust the operation of a layered-forming headbox, where non-uniform filler and fiber Z-distributions can be controlled.

In this way, the sensor arrangement 200 may simultaneously take all of the measurements needed for tomographic imaging of the paper sheet 108. The need for sequential scanning of the paper sheet 108 is avoided so that tomographic imaging of non-stationary targets or targets whose properties are changing dynamically can be performed. Also, the need for sequential focusing of confocal systems to scan through the thickness of the paper sheet 108 is avoided. In addition, since the scattering and absorption of the material(s) in the paper sheet 108 may differ among the multiple wavelengths or wavelength bands employed, the resolving power and measurement uncertainty of the sensor arrangement 200 may differ from that of devices that scan multiple geometries sequentially with the same wavelengths or bands used at all geometries. Employing a set of wavelengths that are close together but non-overlapping, such as can be produced by tunable lasers, may ensure that the scattering or absorption properties of the target are essentially the same for each wavelength.

Although FIG. 2 illustrates one example of a sensor arrangement 200 for Z-structure measurements using simultaneous multi-band tomography, various changes may be made to FIG. 2. For example, the number of radiance sources 202a-202f and sensors 204a-204g are for illustration only. Any suitable number of radiance sources 202a-202f or sensors 204a-204g can be used in the sensor arrangement 200. Also, the positioning of the radiance sources 202a-202f and sensors 204a-204g is for illustration only. The radiance sources 202a-202f and sensors 204a-204g could be positioned in any other suitable manner in the sensor arrangement 200.

Figure 3:
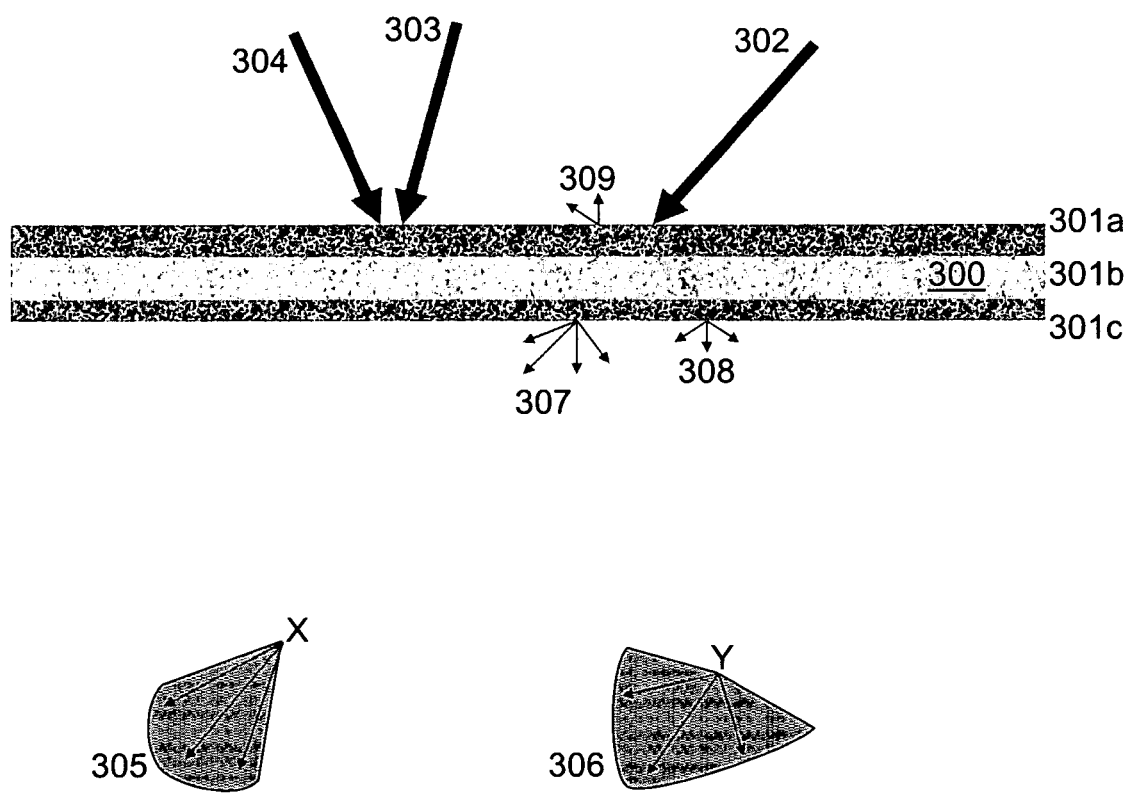
FIG. 3 illustrates an example analysis of Z-structure measurements using simultaneous multi-band tomography according to one embodiment of this disclosure.

FIG. 3 illustrates an example analysis of Z-structure measurements using simultaneous multi-band tomography according to one embodiment of this disclosure. The example analysis shown in FIG. 3 is for illustration only. Z-structure measurements could be analyzed in any other suitable manner. Also, for ease of explanation, the analysis shown in FIG. 3 is described with respect to the sensor arrangement 200 shown in FIG. 2. The analysis could be performed using any other sensor arrangement, device, or system.

As shown in FIG. 3, a sheet 300 contains several distinct layers 301a-301c joined together as a laminate. Collimated narrow beams 302-304 of essentially monochromatic light are incident on the sheet 300, and these beams 302-304 do not contain light of the same wavelength. The beams 302-304 are not all incident on the sheet 300 at the same angle and need not all be incident at the same spot.

The wavelengths of light and materials comprising the sheet 300 are such that scattering may occur to a significant extent within each layer 301a-301c. If there are distinct boundaries between layers 301a-301c, scattering may also occur at a boundary between the layers 301a-301c. Light absorption may also occur to different extents in different layers 301a-301c. This is often the case for visible or infra-red light in fibrous sheets such as paper.

The degree of scattering in any layer may depend on the composition of the layer, and layers with larger amounts of interface area per unit volume may cause more intense scattering than layers with smaller amounts of interface area. The interface area per unit volume in a layer of a paper sheet may be higher if that layer contains hardwood fibers instead of softwood fibers, if it contains a large amount of filler material such as calcium carbonate, or if the filler material exists as fine particles rather than as coarse particles (such as calcium carbonate formed by precipitation rather than by grinding mineral).

As a beam of collimated light propagates through a scattering medium, it is progressively dispersed into a diffuse radiance. The degree of dispersal depends on the scattering power of the medium and on the distance traversed by the radiance within the medium. A collimated beam has all of its power concentrated in a very narrow range of angles, such that its divergence angle is approximately zero. At some position X within a scattering medium, the beam has been partially diffused to a radiance with angular intensity distribution 305. At a position Y further within a scattering medium, the angular intensity distribution is further diffused to an angular distribution 306. Note that, although not depicted in the distributions 305-306, the angular intensity distributions may also contain backscattered light that is propagated at an angle of greater than 90 degrees to the direction of the original collimated beam. At a sufficient depth, the radiance may be fully diffused, such that the angular intensity is essentially uniform.

For a relatively thin sheet 300, the incident collimated beams 302-304 result in excident radiances such as 307-309 over an area of the sheet 300. For any point at which excident radiances are measured, the intensity may vary with the angle of measurement. The angular distribution of intensity at each excident point is determined by the scattering and absorption properties through the sheet 300.

In conventional tomographic measurements, the object to be measured is illuminated at each of several angles of incidence sequentially. For each illumination condition, the intensity of excident light is measured and recorded at multiple angles or locations.

A mathematical model of light propagation through a scattering medium can be formed, and parameters for scattering and absorption can be assigned to regions of the object in the model. Positions may also be assigned to internal boundaries or discontinuities of an object in the model. The excident light intensities for each illumination condition can be computed according to the model. The scattering and absorption parameters in the model and the locations of internal boundaries (if any) can be iteratively adjusted so that the excident light intensities computed according to the model are the closest match to the corresponding recorded light intensities. The closest match may be, for example, the case with the minimum squared difference, minimum weighted squared difference, or minimum greatest difference between computed intensities and recorded intensities.

As a mathematical problem, the algorithm for tomographic computations is often ill-conditioned or indeterminate, in that there may be more than one set of parameters for which the model produces the same set of computed excident light intensities. Accordingly, it is customary to confine the parameters to physically justifiable patterns and to impose certain regularization operations on the parameters. For example, the scattering parameters of the model may be required to be constant or continuous or smooth within regions of the object, or they may be required to be selected within particular ranges of values. Similarly, the internal boundaries may be required to have minimum area or to be geometrically constrained, such as by being confined to planar or spheroidal or other particular shapes.

In accordance with this disclosure, the sheet 300 is illuminated at plural angles of incidence simultaneously, where illumination at each angle of incidence employs a different wavelength or range of wavelengths. The excident light at each wavelength used for illumination is measured simultaneously by light detectors at each of plural angles. The absorption and scattering parameters of the sheet can then be computed from measurements made at a single instant. Regularization of the computation may confine variations in the parameters such that they vary only with Z-depth within the sheet 300 or within a layer 301a-301c of the sheet 300 or that they are constant in each layer 301a-301c of the sheet 300 but may differ between layers 301a-301c of the sheet 300.

Although FIG. 3 illustrates one example of an analysis of Z-structure measurements using simultaneous multi-band tomography, various changes may be made to FIG. 3. For example, although a particular form of sheet 300 was used for illustrative purposes in FIG. 3, this disclosure is clearly not limited to measurements of sheets of that form. For example, the light scattering or light absorption properties of a layer in a sheet need not be the same everywhere in that layer. Similarly, the sheet may include a single layer lacking distinct interior boundaries but having light scattering or light absorption properties that are not the same everywhere in the sheet. As a particular example, while the sheet 300 is shown in FIG. 3 as including distinct homogeneous layers, it could include distinct layers (at least one of which is nonhomogeneous), or it could include a single homogeneous or nonhomogeneous layer. Nonhomogeneous layers may have scattering and absorption properties that vary with depth.

Figure 4:
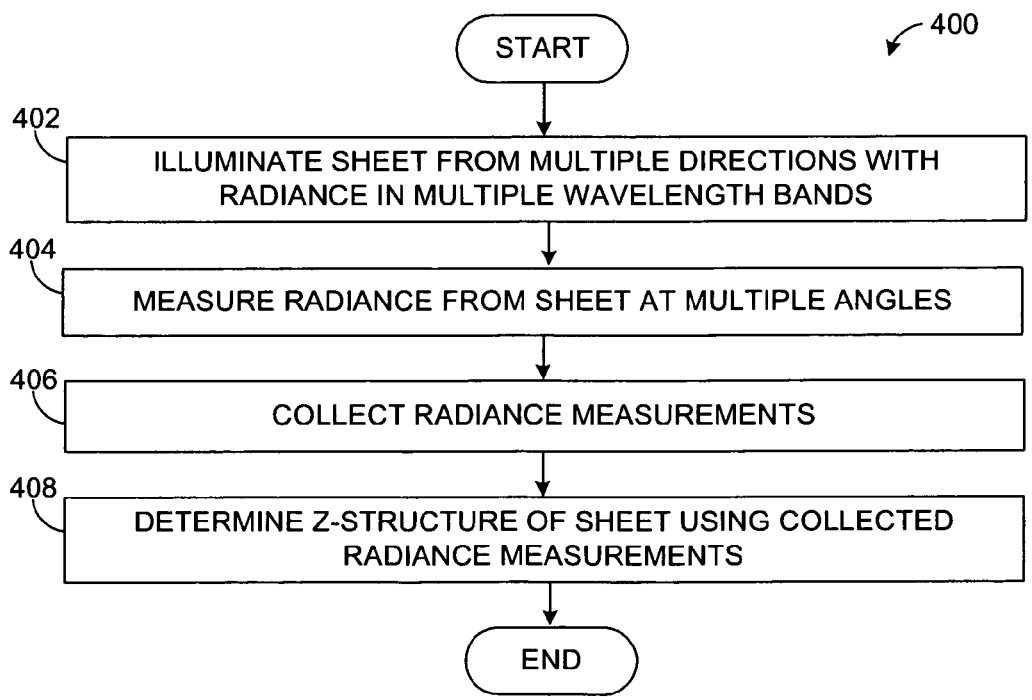
FIG. 4 illustrates an example method for Z-structure measurements using simultaneous multi-band tomography according to one embodiment of this disclosure.

FIG. 4 illustrates an example method 400 for Z-structure measurements using simultaneous multi-band tomography according to one embodiment of this disclosure. The embodiment of the method 400 shown in FIG. 4 is for illustration only. Other embodiments of the method 400 could be used without departing from the scope of this disclosure. Also, for ease of explanation, the method 400 in FIG. 4 is described as being performed by the sensor arrangement 200 of FIG. 2 operating in the system 100 of FIG. 1. The method 400 could be used in any other suitable device and in any other suitable system.

A sheet of material is illuminated from multiple directions with light in multiple wavelength bands at step 402. This may include, for example, the radiance sources 202a-202f generating beams of light, each beam having a unique wavelength or wavelength range. This may also include the radiance sources 202a-202f illuminating the same general area of a paper sheet 108 or other material with the beams of light.

The radiance of the sheet is measured from multiple angles at step 404. This may include, for example, the sensors 204a-204g measuring the radiance from the paper sheet 108 or other material. This may also include each sensor dividing the radiance received from the paper sheet 108 or other material into wavelength bands (such as bands corresponding to the bands of illumination provided by the radiance sources 202a-202f) and measuring the radiance in each wavelength band.

The radiance measurements are collected at step 406. This could include, for example, the sensors 204a-204g transmitting the measured radiance values to the measurement controller 206. Each sensor could transmit the values to the measurement controller 206 in any suitable manner, such as by using a wired or wireless communication link.

The Z-structure of the sheet of material is determined using the collected radiance measurements at step 408. This could include, for example, the measurement controller 206 using the radiance measurements from the sensors 204a-204g to determine a scattering or absorption profile 208 of the paper sheet 108 or other material. The profile 208 can be used, for example, to identify the thicknesses of various layers in the sheet of material. The profile 208 could also be used to identify non-uniformity of fillers in a paper sheet 108. The Z-structure of the sheet could be used for any suitable purpose, such as adjusting the operation of a machine or process producing the sheet of material.

Although FIG. 4 illustrates one example of a method 400 for Z-structure measurements using simultaneous multi-band tomography, various changes may be made to FIG. 4. For example, the method 400 could be repeated a number of times on a moving sheet of material, and the steps of FIG. 4 could overlap (such as when one set of measurements is being processed while another set is being generated).

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The term "program" refers to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method, comprising:
simultaneously illuminating a common area of a sheet of paper using multiple first radiances, the first radiances illuminating the sheet from different directions, each first radiance having a wavelength or wavelength band;
measuring multiple second radiances from the sheet, each second radiance including at least a portion of two or more first radiances that have interacted with the sheet; and
determining an internal structure of the sheet by determining a scattering profile based on the measurements of the second radiances;
wherein no wavelength that is included in the second radiances and that is measured and used to determine the internal structure of the sheet illuminates the common area of the sheet from more than one direction; and
wherein the determined internal structure of the sheet comprises at least one of:
a location of an internal boundary within the sheet between two layers identified by a discontinuity in the scattering profile; and
a non-uniform distribution of a filler in the sheet identified by a smooth variation in the scattering profile.

2. The method of claim 1, wherein:
at least one of the multiple first radiances is disposed on a first side of the sheet and at least one other of the multiple first radiances is disposed on a second side of the sheet; and
at least one of the multiple second radiances is measured from the first side of the sheet and at least one other of the multiple second radiances is measured from the second side of the sheet.

3. The method of claim 1, wherein:
the first radiances include monochrome beams of light; and
each second radiance is associated with at least one of: two or more of the wavelengths and two or more of the wavelength bands.

4. The method of claim 1, wherein measuring the multiple second radiances from the sheet includes simultaneously measuring the multiple second radiances from the sheet.

5. The method of claim 1, wherein measuring the multiple second radiances from the sheet includes:
dividing at least one of the second radiances into multiple bands, each band associated with one of the first radiances; and
measuring a radiance of each band.

6. The method of claim 1, wherein the determined internal structure of the sheet comprises the internal boundary between the two layers within the sheet.

7. The method of claim 1, wherein the determined internal structure of the sheet comprises the non-uniform distribution of the filler in the sheet.

8. The method of claim 1, further comprising adjusting at least one of a machine and a process producing the sheet based on the determined internal structure of the sheet.

9. The method of claim 1, wherein simultaneously illuminating the sheet includes simultaneously illuminating a single area of the sheet using the multiple first radiances.

10. A system, comprising:
a plurality of radiance sources operable to simultaneously illuminate a common area of a sheet of paper using multiple first radiances, the radiance sources arranged to illuminate the sheet from different directions, each first radiance having a wavelength or wavelength band;
a plurality of sensors operable to measure multiple second radiances from the sheet, each second radiance including at least a portion of two or more first radiances that have interacted with the sheet; and
at least one controller operable to determine an internal structure of the sheet by determining a scattering profile based on the measurements of the second radiances, the at least one controller also operable to control the radiance sources such that no wavelength that is included in the second radiances and that is measured and used to determine the internal structure of the sheet illuminates the common area of the sheet from more than one direction;
wherein the at least one controller is operable to determine the internal structure of the sheet by determining at least one of:
a location of an internal boundary within the sheet between two layers identified by a discontinuity in the scattering profile; and
a non-uniform distribution of a filler in the sheet identified by a smooth variation in the scattering profile.

11. The system of claim 10, wherein:
at least one of the radiance sources is positioned on a first side of the sheet and at least one other of the radiance sources is positioned on a second side of the sheet; and
at least one of the sensors is positioned on the first side of the sheet and at least one other of the sensors is positioned on the second side of the sheet.

12. The system of claim 11, wherein:
the radiance sources are angularly distributed non-uniformly around the sheet; and
the sensors are angularly distributed non-uniformly around the sheet.

13. The system of claim 10, wherein:
the first radiances include monochrome beams of light; and
each second radiance is associated with at least one of: two or more of the wavelengths and two or more of the wavelength bands.

14. The system of claim 10, wherein the sensors are operable to measure the second radiances from the sheet simultaneously.

15. The system of claim 10, wherein at least one of the sensors is operable to measure the multiple second radiances from the sheet by:
dividing at least one of the second radiances into multiple bands, each band associated with one of the first radiances; and
measuring a radiance of each band.

16. The system of claim 10, wherein the at least one controller is operable to determine the internal structure of the sheet by identifying the internal boundary between the two layers within the sheet.

17. The system of claim 16, wherein the at least one controller is operable to determine the internal structure of the sheet by identifying the non-uniform distribution of the filler in the sheet.

18. The system of claim 10, wherein the at least one controller is further operable to adjust at least one of a machine and a process producing the sheet based on the determined internal structure of the sheet.

19. The system of claim 10, wherein the radiance sources are operable to simultaneously illuminate a single area of the sheet.

20. A non-transitory computer readable medium embodying a computer program, the computer program comprising:
computer readable program code for controlling a plurality of radiance sources, the radiance sources operable to simultaneously illuminate a common area of a sheet of paper using multiple first radiances, the radiance sources arranged to illuminate the sheet from different directions, each first radiance having a wavelength or wavelength band;
computer readable program code for receiving measurements from a plurality of sensors, the measurements identifying multiple second radiances from the sheet, each second radiance including at least a portion of two or more first radiances that have interacted with the sheet; and computer readable program code for determining an internal structure of the sheet by determining a scattering profile based on the measurements of the second radiances;

wherein the computer readable program code for controlling the radiance sources comprises computer readable program code for controlling the radiance sources such that no wavelength that is included in the second radiances and that is measured and used to determine the internal structure of the sheet illuminates the common area of the sheet from more than one direction; and wherein the computer readable program code for determining the internal structure of the sheet comprises computer readable program code for determining at least one of:

a location of an internal boundary within the sheet between two layers identified by a discontinuity in the scattering profile; and a non-uniform distribution of a filler in the sheet identified by a smooth variation in the scattering profile.

21. A sheet production system, comprising:

a sheet machine operable to at least one of: manufacture and process a sheet of paper; and a sensor arrangement comprising:

a plurality of radiance sources operable to simultaneously illuminate a common area of the sheet using multiple first radiances, the sensor arrangement arranged to illuminate the sheet from different directions, each first radiance having a wavelength or wavelength band;

a plurality of sensors operable to measure multiple second radiances from the sheet, each second radiance including at least a portion of two or more first radiances that have interacted with the sheet; and at least one controller operable to determine an internal structure of the sheet by determining a scattering profile based on the measurements of the second radiances, the at least one controller also operable to control the radiance sources such that no wavelength that is included in the second radiances and that is measured and used to determine the internal structure of the sheet illuminates the common area of the sheet from more than one direction;

wherein the at least one controller is operable to determine the internal structure of the sheet by determining at least one of:

a location of an internal boundary within the sheet between two layers identified by a discontinuity in the scattering profile; and a non-uniform distribution of a filler in the sheet identified by a smooth variation in the scattering profile.

\* \* \* \* \*